(12) United States Patent
Aujila (10) Patent No.: US 10,772,566 B2
(45) Date of Patent: Sep. 15, 2020

(54) MULTI-ELECTRODE CATHETER SPINE AND METHOD OF MAKING THE SAME

(71) Applicant: Biosense Webster (Israel) Ltd., Yokneam (IL)

(72) Inventor: Vishav Aujila, Valencia, CA (US)

(73) Assignee: Biosense Weber (Israel) Ltd., Yokneam (IL)

( * ) Notice: Subject to any disclaimer, the term of this patent is extended or adjusted under 35 U.S.C. 154(b) by 847 days.

(21) Appl. No.: 15/157,179

(22) Filed: May 17, 2016

(65) Prior Publication Data

US 2017/0332970 A1    Nov. 23, 2017

(51) Int. Cl.
*A61B 5/00* (2006.01)
*A61B 34/20* (2016.01)
(Continued)

(52) U.S. Cl.
CPC .......... *A61B 5/6858* (2013.01); *A61B 5/0422* (2013.01); *A61B 18/1492* (2013.01); *A61B 34/20* (2016.02); *A61M 25/005* (2013.01); *A61M 25/0074* (2013.01); *A61B 2017/00526* (2013.01); *A61B 2018/0016* (2013.01); *A61B 2018/00267* (2013.01);
(Continued)

(58) Field of Classification Search
CPC ..... A61B 5/6858; A61B 5/0422; A61B 34/20; A61B 18/1492; A61M 25/005; A61M 25/0074
See application file for complete search history.

(56) References Cited

U.S. PATENT DOCUMENTS 5,228,441 A * 7/1993 Lundquist .......... A61B 18/1492
600/380
5,391,199 A   2/1995 Ben-Haim
(Continued)

FOREIGN PATENT DOCUMENTS

EP    0617916 A1    10/1994
WO    96/05768      2/1996

OTHER PUBLICATIONS

Fort Wayne Materials, Technical Sheets, 2009, Fort Wane Metals Research Products Company, pp. 19-26 (Year: 2009).*
(Continued)

*Primary Examiner* — Linda C Dvorak
*Assistant Examiner* — Annabeth E Rodriguez
(74) *Attorney, Agent, or Firm* — Dergosits & Noah LLP; Todd A. Noah (57) ABSTRACT

A flexible frame comprising an electrically conductive hollow cylindrical metallic tube having a plurality of cuts along the longitudinal axis to form a plurality of conductive wires. The wires are equally spaced apart circumferentially along the longitudinal axis of the tube by a gap to electrically isolate the wires. A first electrode is mounted around the circumference of the frame along the longitudinal axis and attached to a first wire of the plurality of wires. A second electrode is mounted around the circumference of the flexible frame along the longitudinal axis at a predetermined distance from the first electrode and attached to a second wire. A non-conductive thermoplastic layer may be secured to the outer surface of the flexible frame between the first and second electrodes to form an insulation layer between the first and second electrodes.

23 Claims, 7 Drawing Sheets

(51) Int. Cl.
  *A61B 5/042*   (2006.01)
  *A61B 18/14*   (2006.01)
  *A61M 25/00*   (2006.01)
  *A61B 17/00*   (2006.01)
  *A61B 18/00*   (2006.01)

(52) U.S. Cl.
  CPC ............... *A61B 2018/00351* (2013.01); *A61B 2018/00577* (2013.01); *A61B 2034/2051* (2016.02); *A61B 2218/002* (2013.01); *A61B 2562/12* (2013.01)

(56) References Cited

U.S. PATENT DOCUMENTS

| | | | |
|---|---|---|---|
| 5,524,619 A * | 6/1996 | Ouchi | A61B 5/0422 600/373 |
| 5,855,552 A | 1/1999 | Houser et al. | |
| 6,032,077 A | 2/2000 | Pomeranz | |
| 6,064,905 A | 5/2000 | Webster, Jr. et al. | |
| 6,099,524 A | 8/2000 | Lipson et al. | |
| 6,239,724 B1 | 5/2001 | Doron et al. | |
| 6,322,089 B1 | 11/2001 | Dantele et al. | |
| 6,332,089 B1 | 12/2001 | Acker et al. | |
| 6,484,118 B1 | 11/2002 | Govari | |
| 6,618,612 B1 | 9/2003 | Acker et al. | |
| 6,690,963 B2 | 2/2004 | Ben-Haim et al. | |
| 8,518,038 B2 | 8/2013 | Swanson | |
| 8,560,086 B2 | 10/2013 | Just et al. | |
| 8,764,746 B2 | 7/2014 | Podmore et al. | |
| 9,179,971 B2 * | 11/2015 | Kirschenman | A61N 1/056 |
| 2002/0038139 A1 | 3/2002 | Wessman et al. | |
| 2002/0065455 A1 | 5/2002 | Ben-Haim et al. | |
| 2003/0060822 A1 * | 3/2003 | Schaer | A61B 18/1492 606/41 |
| 2003/0120150 A1 | 6/2003 | Govari | |
| 2004/0068178 A1 | 4/2004 | Govari | |
| 2006/0142652 A1 | 6/2006 | Kennan | |
| 2008/0161788 A1 * | 7/2008 | Dando | A61B 18/1492 606/34 |
| 2009/0171274 A1 * | 7/2009 | Harley | A61B 5/0422 604/95.04 |
| 2012/0116392 A1 | 5/2012 | Williard | |
| 2012/0271135 A1 | 10/2012 | Burke et al. | |
| 2012/0271140 A1 * | 10/2012 | Kordis | A61B 5/0422 600/375 |
| 2014/0261985 A1 * | 9/2014 | Selkee | A61M 25/0009 156/187 |
| 2015/0342532 A1 | 12/2015 | Basu et al. | |

OTHER PUBLICATIONS

European Search Report and Written Opinion for European Application No. 17171315.9, dated Oct. 9, 2017.
Extended European Search Report in corresponding European Patent Application No. 19190023.2, dated Nov. 6, 2019.

* cited by examiner

MULTI-ELECTRODE CATHETER SPINE AND METHOD OF MAKING THE SAME

FIELD OF THE PRESENT DISCLOSURE

This disclosure relates generally to methods and devices for percutaneous medical treatment, and specifically to catheters, in particular, multi-electrode catheters. More particularly, this disclosure relates to an improved method of manufacturing multi-electrode diagnostic and treatment catheters.

BACKGROUND

Radiofrequency (RF) electrode catheters have been in common use in medical practice for many years. They are used to stimulate and map electrical activity in the heart and to ablate sites of aberrant electrical activity. Specifically, targeted ablation may be performed for a number of indications. For example, ablation of myocardial tissue is well known as a treatment for cardiac arrhythmias by using a catheter to apply RF energy and create a lesion to break arrhythmogenic current paths in the cardiac tissue. As another example, a renal ablation procedure may involve the insertion of a single or multi-electrode catheter into a renal artery in order to complete a helical or circumferential lesion in the artery in order to denervate the artery for the treatment of hypertension. In other uses, the electrode catheter is inserted into a patient and positioned in a chamber of the heart to determine the location of aberrant electrical activity.

In many instances, the use of a multi-electrode catheter is preferred. Further, catheters are increasingly called upon to perform multiple functions, whether it is diagnostic or therapeutic. Often the catheters serve both functions. The size of the catheter is also a concern. In many instances, a radial insertion point into the patient is preferred over a femoral approach. Also, smaller is usually considered less invasive and less traumatic along the insertion pathway. Therefore, in designing multi-electrode catheters, internal lumen space is at a premium. The lumens may, among other things, house all of the wiring used to connect the electrodes and various sensors to the system controller, as well as function as a conduit for supplying irrigation fluid to the treatment site. Each of these functions that a single catheter performs further increases the demand for space within the lumen.

Accordingly, it would be desirable to provide a multi-electrode catheter that can accommodate more features while maintaining a desirable insertion size. As will be described in the following materials, this disclosure satisfies these and other needs.

SUMMARY

The present disclosure is directed to a catheter, the catheter includes an elongated body and a multi-electrode assembly mounted at a distal end of the elongated body. The multi-electrode assembly includes at least one spine, the at least one spine including a flexible frame, the flexible frame having a plurality of conductive wires and a non-conductive outer layer and a plurality of ring electrodes, wherein each of the plurality of ring electrodes is welded to an adjacent conductive wire of the plurality of conductive wires.

In one aspect, the plurality of conductive wires includes an electrical insulator coating. In one aspect the electrical insulator coating is a parylene coating.

In one aspect, the non-conductive coating is a thermoplastic layer. In one aspect, the thermoplastic layer is a polyether block amide and in another the thermoplastic layer is a reflowed thermoplastic, where the reflowed thermoplastic fills a plurality of gaps between the plurality of conductive wires.

In one aspect, the flexible frame comprises a conductive metal chosen from the group consisting of nickel titanium alloy, stainless steel, platinum and MP35N alloy.

In one aspect, the plurality of electrodes comprise an electrically conductive metal chosen from the group consisting of palladium, platinum, gold, iridium and combinations and alloys thereof.

In one aspect, the multi-electrode assembly is a single spine configured to form a helical-shaped electrode assembly when deployed from the catheter In one aspect, the multi-electrode assembly includes a plurality of spines and in one aspect the plurality of spines are configured to form a basket-shaped electrode assembly when deployed.

This disclosure is also directed to a method for manufacturing a multi-electrode assembly, the method includes forming a flexible frame, the flexible frame comprising a plurality of conductive wires, attaching a plurality of ring electrodes to the flexible frame, wherein attaching the plurality of ring electrodes to the flexible frame includes welding each of the plurality of electrodes to the conductive wire, where each of the plurality of conductive wires has only one electrode electrically attached and forming a thermoplastic layer on at least an outer portion of the flexible frame.

In one aspect, wherein the forming the flexible frame comprises cutting the plurality of conductive wires from a conductive metal cylinder, wherein the plurality of conductive wires are joined at a distal ring. In one aspect, the flexible frame is a conductive metal chosen from the group consisting of nickel titanium alloy, stainless steel, platinum and MP35N alloy In one aspect, the method further includes coating the plurality of conductive wires with a non-conductive coating. The non-conductive coating may be a parylene coating.

In one aspect, forming a thermoplastic layer includes placing a thermoplastic tubing adjacent the plurality of ring electrodes, covering the thermoplastic tubing with a heat shrink tubing and heating the thermoplastic tubing to reflow the thermoplastic to form an outer layer. The thermoplastic tubing is heated to reflow the thermoplastic into a plurality of gaps to electrically isolate a plurality of conductive wires and in another aspect the thermoplastic tubing is heated to reflow the thermoplastic to form a thermoplastic layer on the outer surface of the flexible frame.

In one aspect, the method further includes removing the distal ring from the cut conductive metal cylinder after forming the thermoplastic layer.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a," "an" and "the" include plural referents unless the content clearly dictates otherwise.

Figure 1:
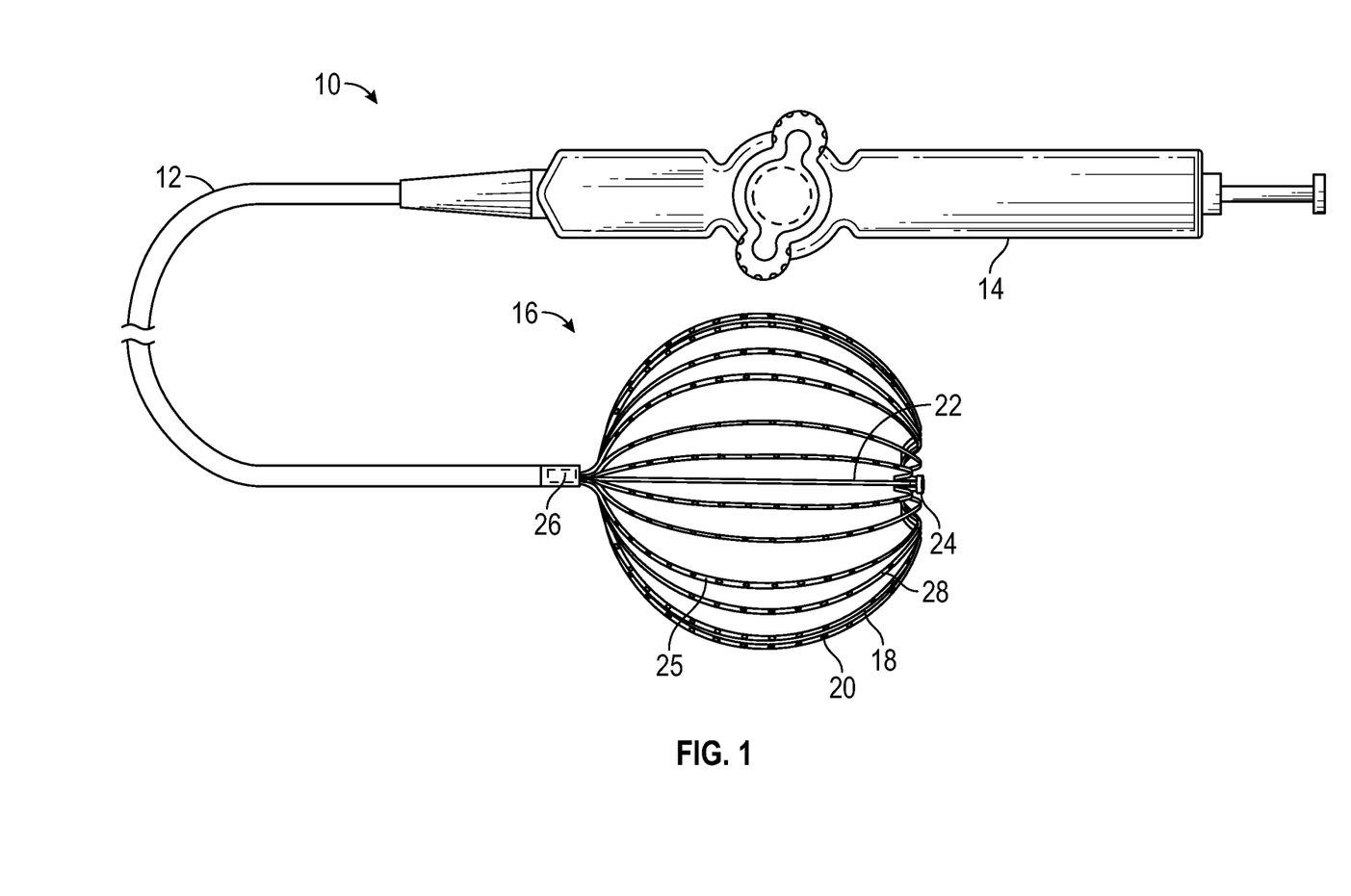
FIG. 1 is a perspective view of a multi-electrode catheter in accordance with an embodiment of the present invention.

As shown in FIG. 1, the catheter 10 comprises an elongated catheter body 12 having proximal and distal ends and a control handle 14 at the proximal end of the catheter body, with a basket-shaped electrode assembly 16 having a plurality of spines 18, each carrying multiple electrodes 20, mounted at the distal end of the catheter body 12. The catheter body 12 comprises an elongated tubular construction having a single, axial or central lumen (not shown), but can optionally have multiple lumens if desired. To enable accurate mapping of electrical signals, for example to detect most or substantially all of the electrical function of the right or left atrium in as little as a single heartbeat, some embodiments may provide an array of electrodes with a relatively high density. As such, numbers of spines 18 employed may be eight, ten, twelve or any other suitable number. Spines 18 may be evenly or unevenly distributed radially. Further, each spine 18 may include multiple electrodes 20, such as at least ten and up to approximately 16 electrodes per spine. In other applications, fewer numbers of spines and/or electrodes may be employed as desired. Further, the electrodes may be evenly distributed along each spine or may be skewed proximally, centrally or distally to facilitate analysis of the measured electrical signals or to access desired regions of the patient's anatomy. In some embodiments, one or more of electrodes 20 may be configured to deliver radio frequency energy to ablate tissue adjacent the electrode.

The catheter body 12 is flexible, i.e., bendable, but substantially non-compressible along its length. The catheter body 12 can be of any suitable construction and made of any suitable material. One construction comprises an outer wall made of polyurethane or PEBAX® (polyether block amide). The outer wall comprises an imbedded braided mesh of stainless steel or the like to increase torsional stiffness of the catheter body 12 so that, when the control handle 14 is rotated, the distal end of the catheter body will rotate in a corresponding manner. The outer diameter of the catheter body 12 is not critical, but generally should be as small as possible and may be no more than about 10 french depending on the desired application. Likewise, the thickness of the outer wall is not critical, but may be thin enough so that the central lumen can accommodate a pulling member wire, lead wires, sensor cables and any other wires, cables or tubes. If desired, the inner surface of the outer wall is lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

The basket-shaped electrode assembly 16 may also include a pulling member 22 that is generally coaxial with the catheter body 12 and extends from the proximal end of catheter body 12 through the central lumen and is attached to a structural element, such as cap 24, to couple pulling member 22 to the distal ends of spines 18. The pulling member 22 is afforded longitudinal movement relative to the catheter body so that it can move the distal ends of the spines 18 proximally relative to the catheter body 12 to radially expand the electrode assembly. In some embodiments, spines 18 may have a preshaped expanded configuration that they assume when unconstrained, and do not require a pulling member. The proximal ends of spines 18 may be received by another structural element disposed within catheter body 12, such as collar 26 as schematically indicated in FIG. 1. As will be described in further detail below, collar 26 may secure and maintain the proximal ends of spines 18 in a desired radial configuration with respect to each other.

Since the proximal ends of spines 18 are secured to the catheter body 12 by collar 26, the distance between the distal and proximal ends of spines 18 shortens when they bow outwards into an expanded arrangement, which may be associated with relative movement of pulling member 22 in the proximal direction. Alternatively or in addition, spines 18 may include a material as described below that facilitates assuming the expanded arrangement, such as a shape memory material, so that pulling member 22 aids the transition between the expanded and collapsed arrangements or is unnecessary. In an embodiment, the pulling member 22 may comprise a wire or hypotube formed from a suitable shape memory material, such as a nickel titanium alloy as described below. As will be appreciated, different relative amounts of movement of the pulling member 22 along the longitudinal axis may affect the degree of bowing, such as to enable the spines 18 to exert greater pressure on the atrial tissue for better contact between the tissue and the electrodes on the spines. Thus, a user can modify the shape of the electrode assembly by adjusting the distance pulling member 22 is withdrawn when basket-shaped electrode assembly 16 assumes an expanded arrangement.

A range of travel of pulling member 22 from its most distal location to a relatively more proximal location corresponds to deflection of basket-shaped electrode assembly 16 from a collapsed arrangement to an expanded arrangement having the generally spherical shape shown in FIG. 1. When in the collapsed arrangement, the spines may be constrained, such as by a guiding sheath, and may be deflected from the collapsed arrangement to the first expanded deployed configuration by withdrawing the guiding sheath and imparting sufficient force to pulling member 22. As will be appreciated, in the collapsed arrangement, spines 18 assume a generally linear alignment with the catheter body 12 to minimize the outer diameter for insertion within and withdrawal from the patient. In expanding to an expanded arrangement, spines 18 of basket-shaped electrode assembly 16 bow outwards. When positioned at a desired location within a patient, assuming an expanded arrangement may bring electrodes 20 into contract or closer proximity with the walls of the chamber or other region in which basket-shaped electrode assembly 16 is positioned. The overall size of basket-shaped electrode assembly 16 may be selected based on the patient's anatomy to provide a close fit to the area of the patient being investigated or treated, such as the right or left atria. In some embodiments, pulling member 22 may be coupled to an actuator on control handle 14, which may be a sliding lever, a rotating knob or any other suitable implementation. As such, the actuator may be used to adjust the relative longitudinal position of pulling member 22 and in particular may be configured adjust the position of pulling member 22 to achieve one or more desired expanded arrangements of basket-shaped electrode assembly 16.

Basket-shaped electrode assembly 16 may be constructed by employing a framework of a suitable substrate material. In one aspect, a shape memory material may be used to aid assuming the expanded and collapsed arrangements. For example, nickel-titanium alloys known as nitinol may be used. At body temperature, nitinol wire is flexible and elastic and, like most metals, nitinol wires deform when subjected to minimal force and return to their shape in the absence of that force. Nitinol belongs to a class of materials called Shaped Memory Alloys (SMA) that have interesting mechanical properties beyond flexibility and elasticity, including shape memory and superelasticity which allow nitinol to have a "memorized shape" that is dependent on its temperature phases. The austenite phase is nitinol's stronger, higher-temperature phase, with a simple cubic crystalline structure. Superelastic behavior occurs in this phase (over a 50°–60° C. temperature spread). Correspondingly, the martensite phase is a relatively weaker, lower-temperature phase with a twinned crystalline structure. When a nitinol material is in the martensite phase, it is relatively easily deformed and will remain deformed. However, when heated above its austenite transition temperature, the nitinol material will return to its pre-deformed shape, producing the "shape memory" effect. The temperature at which nitinol starts to transform to austenite upon heating is referred to as the "As" temperature. The temperature at which nitinol has finished transforming to austenite upon heating is referred to as the "Af" temperature. Accordingly, basket-shaped electrode assembly 16 when formed from such materials may have a three dimensional shape that can be easily collapsed to be fed into a guiding sheath and then readily returned to its expanded shape memory configuration upon delivery to the desired region of the patient upon removal of the guiding sheath and/or actuation of pulling member 22.

As will be recognized by one skilled in the art, the number of spines 20 can vary as desired depending on the particular application, so that the basket assembly has at least two spines, and as many as ten, twelve or more spines. As used herein, the term "basket-shaped" in describing the electrode assembly 16 is not limited to the depicted configuration, but can include other designs, such as egg-shaped designs, that include a plurality of expandable arms connected, directly or indirectly, at their proximal and distal ends. Those skilled in the art will further appreciate that the methods discussed below will equally apply to multi-electrode catheters that do not form a basket.

Figure 2:
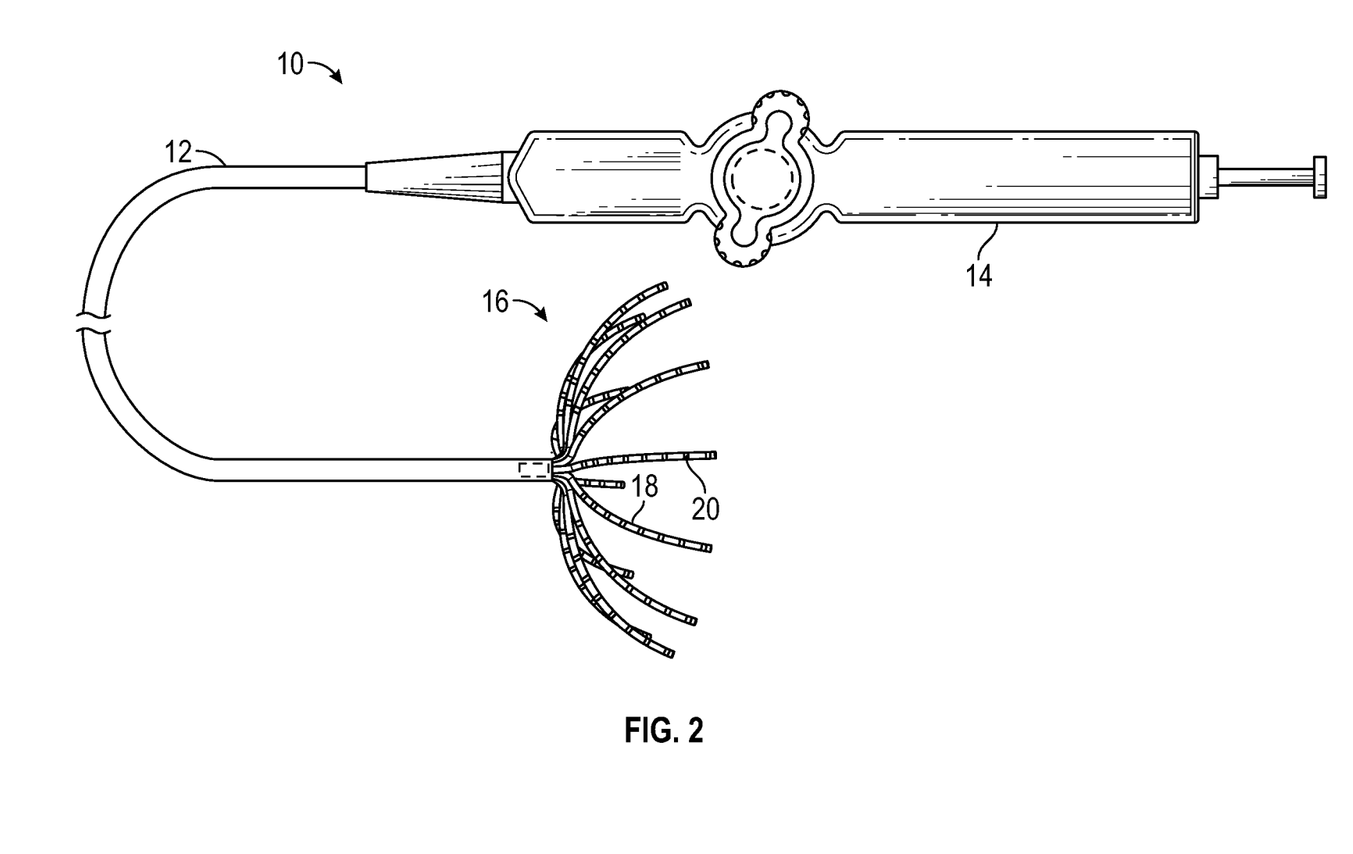
FIG. 2 is a perspective view of a multi-electrode catheter in accordance with an embodiment of the present invention.

For example, the electrode assembly 16 may employ a configuration such as the multi-spine assembly shown in FIG. 2. In this embodiment, the electrode assembly 16 may include a plurality of expandable spines 18 connected to the distal end of the catheter body 12, directly or indirectly, at their proximal ends only and not at their distal ends. Catheter 10 comprises an elongated catheter body 12 having proximal and distal ends, a control handle 14 at the proximal end of the catheter body 12, and an electrode assembly 16 having a plurality of spines 18, having free distal ends and secured at their proximal end to catheter body 12. To enable accurate mapping of electrical signals, for example to detect most or substantially all of the electrical function of the right or left atrium in as little as a single heartbeat, some embodiments may provide an array of electrodes with a relatively high density. As such, numbers of spines 18 employed may be eight, ten, twelve or any other suitable number. Spines 18 may be evenly or unevenly distributed radially. Further, each spine 18 may include multiple electrodes 20, such as at least ten and up to approximately 16 electrodes per spine. In other applications, fewer numbers of spines and/or electrodes may be employed as desired. Further, the electrodes may be evenly distributed along each spine or may be skewed proximally, centrally or distally to facilitate analysis of the measured electrical signals or to access desired regions of the patient's anatomy. In some embodiments, one or more of electrodes 20 may be configured to deliver radio frequency energy to ablate tissue adjacent the electrode.

Figure 3:
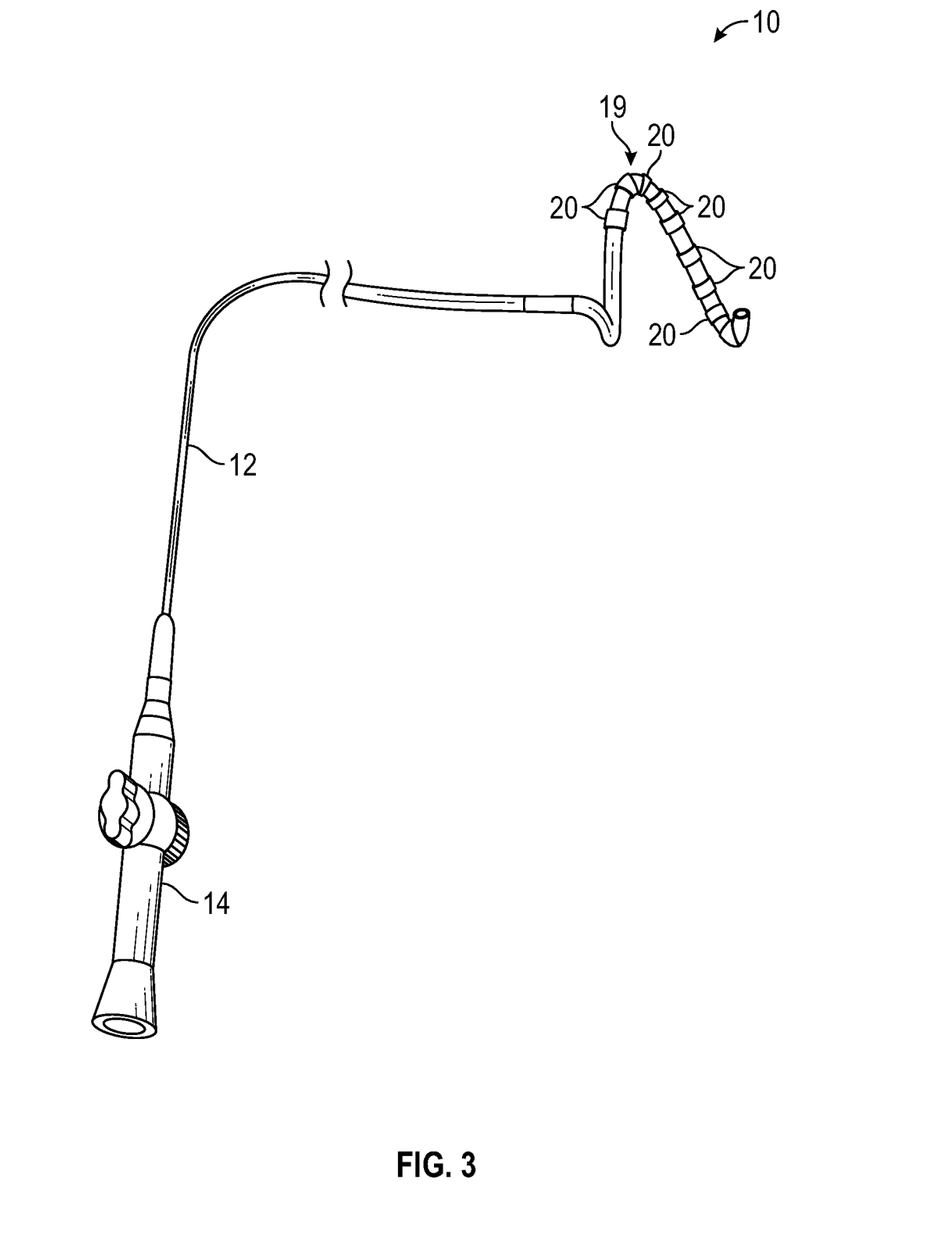
FIG. 3 is a perspective view of a multi-electrode catheter in accordance with an embodiment of the present invention.

In another embodiment, the electrode assembly 16 may employ a configuration such as a helical or lasso shaped multi-electrode catheter as shown in FIG. 3. In this embodiment, catheter 10, comprises an elongated body that includes an insertion shaft or catheter body 12 having a longitudinal axis, and an intermediate section 19 distal of the catheter body. In this embodiment, a series of ring electrodes 20 are disposed along the length of intermediate section 19. Electrodes 20 are adapted for contact with target tissue. In this embodiment, intermediate section 19 forms a helical shape once it is deployed at the treatment site. In this embodiment, intermediate section 19 may include multiple electrodes 20, such as at least ten and up to approximately 16 electrodes, that form a helical lesion pattern when activated. All other aspects of this embodiment are similar to those stated above for the embodiment illustrated in FIGS. 1 and 2. In this embodiment the catheter may be 8, 9, 11, or 12 French.

In a multi-electrode catheter having one to a plurality of spines, one of skill in the art will appreciate that space is at a premium within the catheter lumen. Internal lumens may be used for multiple purposes, such as, for example, a conduit for irrigation fluid as well as a conduit for running electrical connections from the distal end to the control handle. In some embodiments, a catheter lumen is used to house the wires that connect electrodes to a system controller. As the number of electrodes increases, the space demand also increases. FIG. 4 to FIG. 8 illustrate a method for manufacturing a multi-electrode flexible frame that reduces the number of wires within a lumen by creating a conductive flexible frame to replace at least a portion of the wires that are in prior art devices. An exemplary spine 18 from the basket-shaped multi-electrode device of FIG. 1 will be used to illustrate this method.

Generally, referring back to FIG. 1, each spine 18 comprises an electrically conductive flexible frame 25 with a non-conductive covering 28 on which one or more ring electrodes 20 are mounted. In a preferred embodiment, the flexible frame 25 each comprise a Nitinol® cylinder and the non-conductive coverings 28 each comprise a biocompatible thermoplastic, such as PEBAX® polyether block amide.

Figure 4:
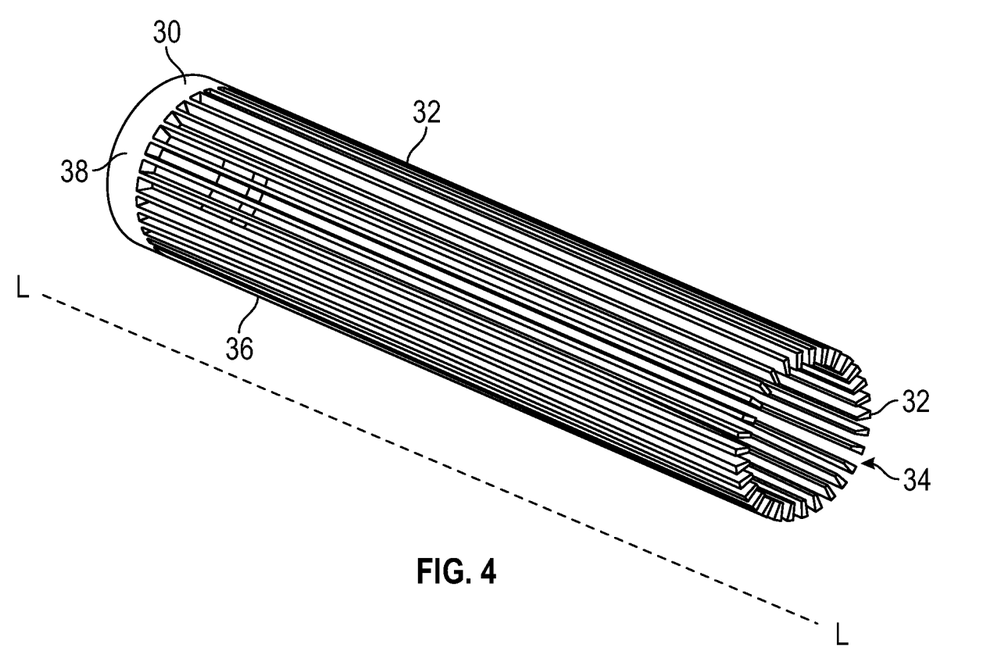
FIG. 4 is a perspective view of a laser cut frame, in accordance with an embodiment of the present invention.
Figure 5:
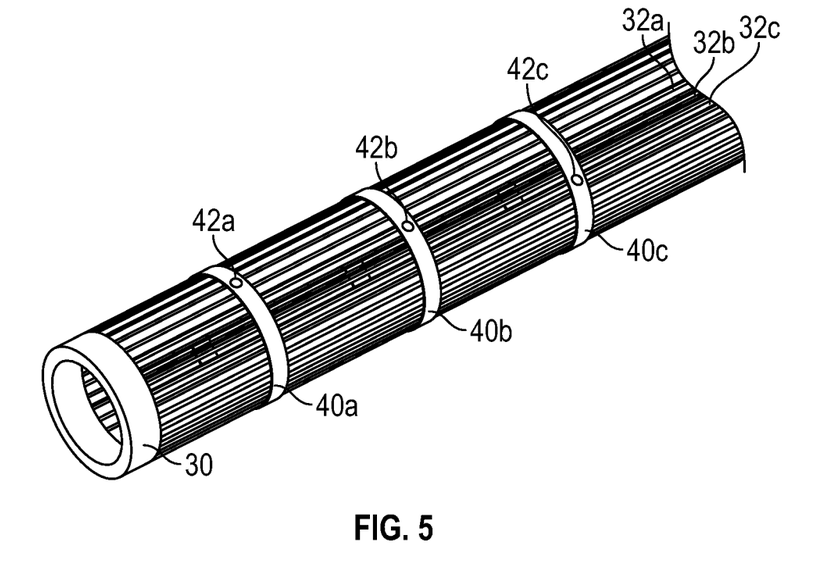
FIG. 5 is a perspective view of the laser cut frame of FIG. 4 with multiple electrodes, in accordance with an embodiment of the present invention.
Figure 7:
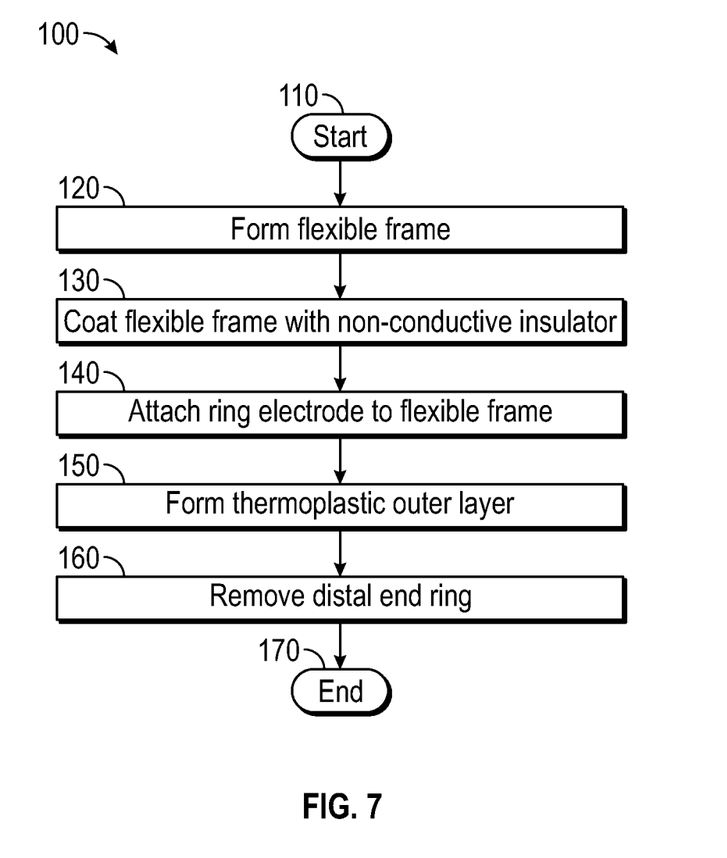
FIG. 7 is a flow chart illustrating one embodiment of a method of manufacturing a multi-electrode spine, in accordance with an embodiment of the present invention.

Referring now to FIG. 7, a method 100 of manufacturing a multi-electrode device begins at Step 110. At Step 120, a flexible frame 25 is formed. The manufacture of each flexible frame 25 begins with a metal cylinder 30 having a longitudinal axis along the line L-L as shown in FIG. 5. The metal cylinder 30 comprises a material that is electrically conductive such as, for example, stainless steel, platinum or MP35N alloy. The outer diameter of metal cylinder may be 0.5 mm to 2 mm, the wall thickness of this cylinder could range from 0.05 mm to 0.25 mm. The length of the metal cylinder may be 50 mm to 100 cm. The metal cylinder 30 is then cut into flexible frame 25. FIG. 4 illustrates one embodiment of a flexible frame 25 cut from a metal cylinder 30. Metal cylinder 30 is cut, using a laser or other equivalent device, into a plurality of straight conductive wires 32. Metal cylinder 30 may be cut into any number of conductive wires based on such factors as the diameter of the metal cylinder and the specific purpose of the multi-electrode device. As an example, metal cylinder may be cut into as few as eight conductive wires and as many as 50 conductive wires. As FIG. 4 illustrates, metal cylinder 30 is not completely cut along its length, leaving a ring of material 38 at a distal end. This ring of material 38 is a temporary ring that is used to keep the plurality of conductive wires separated and aligned throughout this manufacturing process. The plurality of wires 32 and ring of material 38 form the flexible frame 25.

The wires 30 of flexible frame 25 are spaced equally around the circumference of the metal cylinder 30. In one embodiment, each wire 32 is approximately twenty microns wide. Conductive wires 32 may range in width from 50 to 250 microns. FIG. 4 further illustrates that between each wire is a space or gap 34. Gap 34 is used to electrically isolate each conductive wire 32. To further isolate each conductive wire 32, in one embodiment, each wire of the flexible frame 25 is coated with a non-conductive insulator 36, Step 130. In one embodiment the non-conductive insulator 36 is a parylene coating. In another embodiment, the flexible frame is not coated with the non-conductive coating.

Next, at Step 140, a plurality of ring electrodes 40 is attached to flexible frame 25. Referring now to FIG. 5, ring electrodes 40 may be made of any suitable electrically-conductive material, such as palladium, platinum, gold, iridium and combinations and alloys thereof, including, Pd/Pt (e.g., 80% Palladium/20% Platinum) and Pt/Ir (e.g., 90% Platinum/10% Iridium). Ring electrode 40 has an inner diameter dimensioned to slidingly fit over the flexible frame 25. The number of ring electrodes to be attached to the flexible frame 25 may vary based on the use of the multi-electrode catheter. Additionally, the spacing between electrodes may also vary. In one embodiment, electrodes 40 are positioned 1 mm apart. In another embodiment, electrodes 40 are spaced between 1 mm and 15 mm apart. Spacing larger than 15 mm may be used if the application requires it. In another embodiment, the spacing of the ring electrodes may vary on a single spine.

Generally speaking, the flexible frame 25 may support as many ring electrodes as there are conductive wires. As an example, FIG. 5 illustrates a flexible frame 25 having thirty conductive wires 32. Therefore, as many as thirty ring electrodes 40 may be attached to the flexible frame. For the sake of clarity, FIG. 5 illustrates three electrodes 40 attached to flexible frame 25. Each electrode 40 is slide over flexible frame 25 and positioned for attachment to the frame. In one embodiment, to position each electrode 40, a keyhole opening 42 in the electrode is lined up with a single conductive wire 32. The electrode 40 is then attached to the conductive wire by laser welding through the keyhole opening 42. As an example, keyhole opening 42a is used to line up electrode 40a with conductive wire 32a. Once the opening 42a is lined up with wire 32a, the electrode 40a is laser welded through opening 42a to the wire. Similarly, electrodes 40b and 40c are attached to conductive wires 32b and 32c, respectively, through keyhole openings 42b and 42c. Welding the electrode 40 to the conductive wire 32 removes the non-conductive insulator 36 from the conductive wire adjacent to the keyhole opening 42. In another embodiment, each electrode 40 may be attached to a single conductive wire 32 by a resistance welding procedure, which is known in the art.

Figure 6:
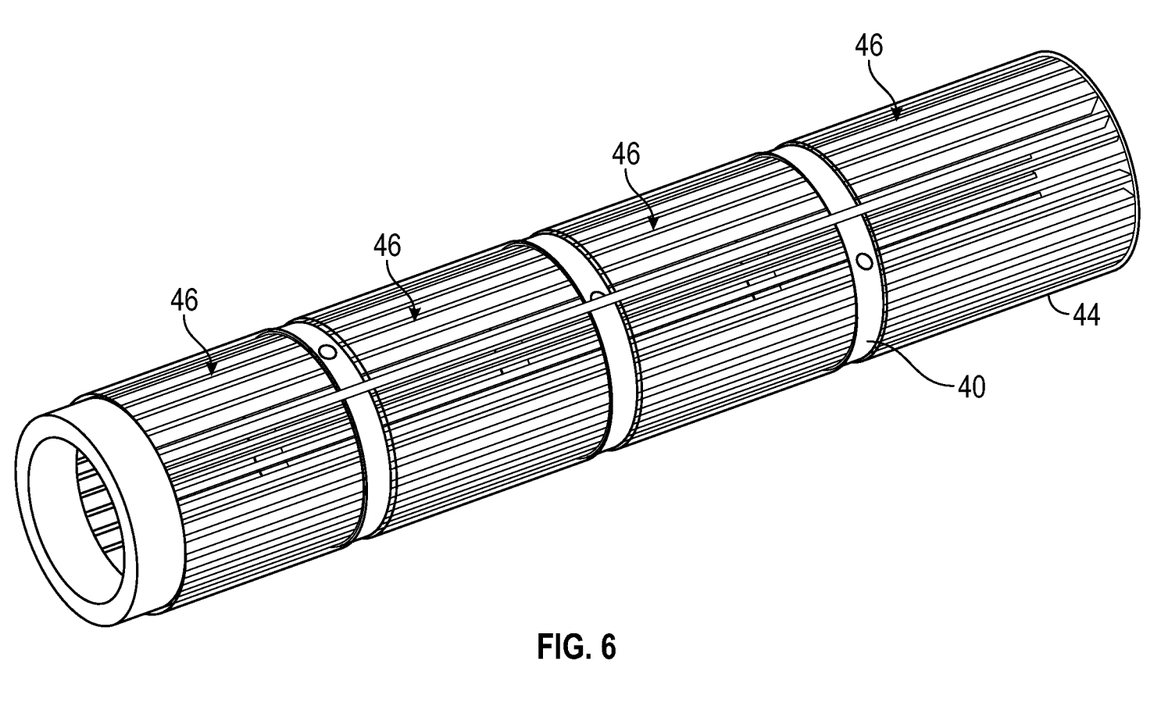
FIG. 6 is a perspective view of the laser cut frame with multiple electrodes of FIG. 5 including a thermoplastic covering, in accordance with an embodiment of the present invention.

The method continues, at Step 150, by forming a thermoplastic outer layer on at least a portion of the flexible frame 25. FIG. 6 illustrates flexible frame 25 having an outer thermoplastic layer 44. In one embodiment, portions of thermoplastic tubing 46, such as, PEBAX® polyether block amide, are place between the electrodes 40. The thermoplastic tubing does not cover the electrodes. This thermoplastic tubing is then covered by heat shrink tubing and hot air is applied to melt and reflow the thermoplastic. In one embodiment, the thermoplastic is heated to reflow the thermoplastic over the outer surface of the flexible frame. In another embodiment, the thermoplastic is heated to reflow the thermoplastic to cover the outer surface and to flow between the conductive wires 32, to at least partially fill the gaps 34 between the wires 32 and to further electrically isolate the individual wires so that the wires do not touch.

After the thermoplastic outer layer is formed, the distal ring of material 30 is removed, at Step 160. Removing the distal ring completely electrically isolates each of the conductive wires of the flexible frame 25. The method of manufacture ends at Step 170.

Figure 8:
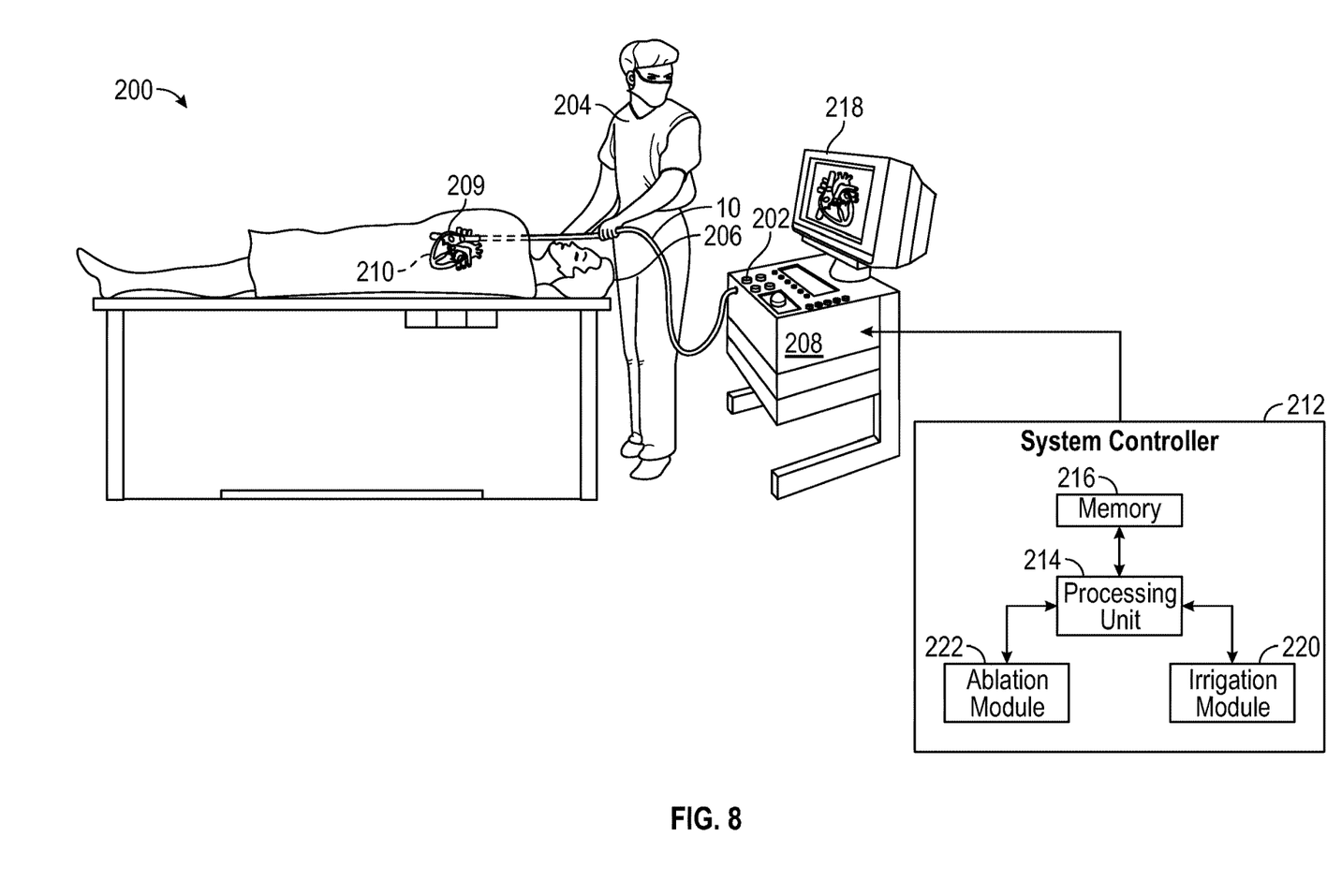
FIG. 8 is a schematic illustration of a system for treating a patient, in accordance with an embodiment of the present invention.

One with skill in the art will appreciate that additional steps may be followed to incorporate the multi-electrode spine manufactured and illustrated in FIGS. 4 to 8. For example, in one embodiment, a plurality of manufactured spines are joined together to form the basket-shaped electrode assembly, like the one illustrated in FIG. 1. In another example, the basket-shaped electrode assembly may be configured to map a chamber of the heart. In an embodiment, as shown in FIG. 2, the electrode assembly 16 may include a plurality of expandable spines connected to the distal end of the catheter body at their proximal ends only and not at their distal ends. In another embodiment, as shown in FIG. 3, a single spine may be used to construct a helical-shaped electrode assembly for ablating vessels, such as a renal artery. In yet another embodiment, a single spine may be used to form a lasso-shaped ablation catheter for ablating, for example, pulmonary vein ostia. In each of these embodiments, the proximal ends of the conductive wires are electrically connected to system 200 as illustrated in FIG. 8 and described below.

As will be appreciated, the catheters mentioned above will include additional structures not described or illustrated for the sake of clarity. For example, a multi-electrode ablation catheter 10 will include those structures necessary for ablation such as a conduit for receiving an RF coil to be used to energize electrodes 40. Other conduits may be used for any suitable purpose, including routing and/or anchoring safety wire to facilitate retrieval of the electrode assembly or other distal portions of catheter 10 should they become detached during a procedure. Safety wire may be formed from Vectran™ or other suitable materials. In other embodiments, one or more conduits may accommodate electromagnetic position sensors that may be used in conjunction with a mapping system to aid visualization of the placement of the distal end of catheter 10 within a patient's anatomy.

Use of multi-electrode catheter 10 in an ablation procedure may follow techniques known to those of skill in the art. FIG. 8 is a schematic, pictorial illustration of a system 200 for renal and/or cardiac catheterization and ablation, in accordance with an embodiment of the present invention. System 200 may be based, for example, on the CARTO™ mapping systems, produced by Biosense Webster Inc. (Diamond Bar, Calif.) and/or SmartAblate or nMarq RF generators. This system comprises an invasive probe in the form of catheter 10 and a control and/or ablation console 202. An operator 204, such as a cardiologist, electrophysiologist or interventional radiologist, inserts ablation catheter 10 into and through the body of a patient 206, such as through a femoral or radial access approach, so that a distal end of catheter 10, in particular, electrode 20, engages tissue at a desired location or locations, such as a chamber of heart 209 of patient 206. Catheter 10 is typically connected by a suitable connector at its proximal end to console 202. Console 202 comprises a RF generator 208, which supplies high-frequency electrical energy via the catheter for ablating tissue 210 at the locations engaged by electrode 20.

Console 202 may also use magnetic position sensing to determine position coordinates of the distal end of catheter 10 inside the body of the patient 206. For this purpose, a driver circuit in console 202 drives field generators to generate magnetic fields within the body of patient 206. Typically, the field generators comprise coils, which are placed below the patient's torso at known positions external to the patient. These coils generate magnetic fields in a predefined working volume that contains the area of interest. A magnetic field sensor (not shown) within distal end of catheter 10 generates electrical signals in response to these magnetic fields. A signal processor in console 202 may process these signals in order to determine the position coordinates of the distal end, typically including both location and orientation coordinates. This method of position sensing is implemented in the above-mentioned CARTO system and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Console 202 may include system controller 212, comprising a processing unit 214 communicating with a memory 216, wherein is stored software for operation of system 200. Controller 212 may be an industry standard personal computer comprising a general purpose computer processing unit. However, in some embodiments, at least some of the functions of the controller are performed using custom designed application specific integrated circuits (ASICs) or a field programmable gate array (FPGA). Controller 212 is typically operated by the operator 204 using suitable input peripherals and a graphic user interface (GUI) 218 which enable the operator to set parameters of the system 200. GUI 218 typically also displays results of the procedure to the operator. The software in memory 216 may be downloaded to the controller in electronic form, over a network, for example. Alternatively or additionally, the software may be provided on non-transitory tangible media such as optical, magnetic or electronic storage media. In some embodiments, one or more contact force sensors may send signals to console 202 to provide an indication of the pressure on electrode 20. Signals from contact force sensor wires may be provided to system controller 212 to obtain measurements from strain gauge. Such signals may be used to provide to the physician the level of tissue contact of each individual electrode. Additionally, the system controller 212 will provide an indication as to which of the multi-electrodes are in contact with the tissue to be ablated. With this feedback information, the practitioner will be able to make the necessary adjustments to ensure a complete ablation. As noted above, this invention is well suited for any multi-electrode catheter such as, for example, those having a lasso, arcuate, helical or basket configuration of ring electrodes.

Typically, during an ablation, heat is generated by the RF energy in the tissue of the patient to effect the ablation and some of this heat is reflected to the electrode 20 causing coagulation at and around the electrode. System 200 irrigates this region through irrigation apertures and the rate of flow of irrigation is controlled by irrigation module 220 and the power (RF energy) sent to electrode 20 is controlled by ablation module 222. Further, the percentage of the surface of electrode 22 that is coupled with tissue may be estimated based on the contact force observed. As yet another example, additional sensors of catheter 10 may provide intracardiac electrocardiograms to system controller 212, to be used for determining when the tissue site being ablated is no longer conducting arrhythmogenic currents.

Described herein are certain exemplary embodiments. However, one skilled in the art that pertains to the present embodiments will understand that the principles of this disclosure can be extended easily with appropriate modifications to other applications.

What is claimed is:

1. An electrically conductive flexible frame comprising:
   an electrically conductive hollow cylindrical metallic tube having an outer surface, a circumference and a longitudinal axis, the cylindrical metallic tube having a plurality of cuts along the longitudinal axis to form the flexible frame comprising a plurality of parallel conductive wires, the plurality of parallel conductive wires remaining parallel along the entire longitudinal axis of the cylindrical metallic tube, each of the plurality of conductive wires being equally spaced apart circumferentially along the longitudinal axis of the tube by a gap to electrically isolate the plurality of wires;

a first electrode mounted around the circumference of the flexible frame along the longitudinal axis of the tube and attached to a first wire of the plurality of conductive wires;

a second electrode mounted around the circumference of the flexible frame along the longitudinal axis of the tube at a predetermined distance from the first electrode and attached to a second wire of the plurality of conductive wires, the second wire being adjacent to the first wire and not attached to the first wire; and a non-conductive thermoplastic layer secured to the outer surface of the flexible frame between the first and second electrodes, such that the thermoplastic layer circumferentially surrounds the plurality of conductive wires to form an insulation layer between the first and second electrodes.

2. The frame of claim 1, wherein each of the plurality of conductive wires includes a non-conductive electrical insulator coating.

3. The frame of claim 2, wherein the electrical insulator coating comprises parylene.

4. The frame of claim 1, wherein the thermoplastic layer comprises a polyether block amide.

5. The frame of claim 1, wherein the thermoplastic layer comprises a reflowed thermoplastic, wherein the reflowed thermoplastic fills each of the gaps between the plurality of conductive wires.

6. The frame of claim 1, wherein the cylindrical metallic tube comprises a conductive metal chosen from the group consisting of nickel titanium alloy, stainless steel, platinum and MP35N alloy.

7. The frame of claim 1, wherein the electrodes comprise an electrically conductive metal chosen from the group consisting of palladium, platinum, gold, iridium and combinations and alloys thereof.

8. The frame of claim 1, wherein the number of the plurality of parallel conductive wires is between 8 and 50.

9. The frame of claim 1, wherein each of the plurality of conductive wires has a width between 50 and 250 microns.

10. The frame of claim 1, wherein each of the plurality of conductive wires has a width of approximately 20 microns.

11. The frame of claim 1, wherein the first electrode includes a first keyhole for attaching the first electrode to the first wire of the plurality of conductive wires and the second electrode includes a second keyhole for attaching the second electrode to the second wire of the plurality of conductive wires.

12. The frame of claim 11, wherein the first electrode is attached to the first wire of the plurality of conductive wires by a first weld through the first keyhole in the first electrode and the second electrode is attached to the second wire of the plurality of conductive wires by a second weld through the second keyhole in the second electrode.

13. The frame of claim 1, wherein the plurality of cuts of the cylindrical metallic tube along the longitudinal axis are made by laser cutting.

14. A method of manufacturing an electrically conductive flexible frame, the method comprising:

cutting an electrically conductive hollow cylindrical metallic tube along a longitudinal axis of the tube to form a plurality of cuts along the longitudinal axis, the plurality of cuts forming the flexible frame comprising a plurality of parallel conductive wires, the plurality of parallel conductive wires remaining parallel along the entire longitudinal axis of the cylindrical metallic tube, each of the plurality of conductive wires being equally spaced apart circumferentially along the longitudinal axis of the tube by a gap to electrically isolate the plurality of conductive wires;

attaching a first electrode around the circumference of the flexible frame along the longitudinal axis of the tube to a first wire of the plurality of conductive wires;

attaching a second electrode around the circumference of the flexible frame along the longitudinal axis of the tube to a second wire of the plurality of conductive wires, the second wire being adjacent to the first wire and the second electrode being located a predetermined distance from the first electrode along the longitudinal axis of the tube and not attached to the first conductive wire;

forming a non-conductive thermoplastic layer on at least an outer surface of the flexible frame between the first and second electrodes, such that the thermoplastic layer circumferentially surrounds the plurality of conductive wires to form an insulation layer between the first and second electrodes.

15. The method of claim 14, further comprising coating the plurality of conductive wires with a non-conductive coating.

16. The method of claim 15, wherein the non-conductive coating comprises parylene.

17. The method of claim 14, wherein the cylindrical metallic tube comprises a metal chosen from the group consisting of nickel titanium alloy, stainless steel, platinum and MP35N alloy.

18. The method of claim 14, wherein forming the non-conducting thermoplastic layer comprises:

placing a thermoplastic tubing around the circumference of the flexible frame in between the first and second electrodes;

covering the thermoplastic tubing with a heat shrink tubing;

heating the thermoplastic tubing to reflow the thermoplastic tubing to form an outer layer.

19. The method of claim 18, wherein the thermoplastic tubing is heated to reflow the thermoplastic tubing into the plurality of gaps between the plurality of wires to electrically isolate a plurality of conductive wires.

20. The method of claim 18, wherein the thermoplastic tubing is heated to reflow the thermoplastic tubing to form a thermoplastic layer on the outer surface of the flexible frame.

21. The method of claim 14, wherein the first electrode includes a first keyhole for attaching the first electrode to the first wire of the plurality of wires and the second electrode includes a second keyhole for attaching the second electrode to the second wire of the plurality of wires.

22. The method of claim 21, wherein the first electrode is attached to the first wire of the plurality of conductive wires by welding through the keyhole in the first electrode and the second electrode is attached to the second wire of the plurality of conductive wires by welding through the keyhole in the second electrode.

23. The method of claim 14, wherein the plurality of cuts of the cylindrical metallic tube along the longitudinal axis are made by laser cutting.

* * * * *